United States Patent
Faverzani

(10) Patent No.: US 11,460,426 B2
(45) Date of Patent: Oct. 4, 2022

(54) METHOD AND APPARATUS FOR DETECTING METAL PARTICLES PRESENT IN A WALL OF A GLASS CONTAINER

(71) Applicant: BORMIOLI PHARMA S.P.A., Milan (IT)

(72) Inventor: Davide Faverzani, Fidenza (IT)

(73) Assignee: BORMIOLI PHARMA S.P.A., Milan (IT)

( * ) Notice: Subject to any disclaimer, the term of this patent is extended or adjusted under 35 U.S.C. 154(b) by 917 days.

(21) Appl. No.: 16/307,766

(22) PCT Filed: Jun. 28, 2017

(86) PCT No.: PCT/IB2017/053875
§ 371 (c)(1),
(2) Date: Dec. 6, 2018

(87) PCT Pub. No.: WO2018/002845
PCT Pub. Date: Jan. 4, 2018

(65) Prior Publication Data
US 2019/0257776 A1      Aug. 22, 2019

(30) Foreign Application Priority Data
Jun. 30, 2016   (IT) .................. 102016000068208

(51) Int. Cl.
*G01N 25/72* (2006.01)
*G01N 33/38* (2006.01)
*B29C 49/80* (2006.01)

(52) U.S. Cl.
CPC ........... *G01N 25/72* (2013.01); *G01N 33/386* (2013.01); *B29C 49/80* (2013.01)

(58) Field of Classification Search
CPC .. G01N 25/72; G01N 33/386; G01N 33/0016; B29C 49/80; C03B 27/044; C03B 27/012; C03B 27/0413
See application file for complete search history.

(56) References Cited

U.S. PATENT DOCUMENTS 2,764,015 A * 9/1956 Menoher ................ G01N 25/72
374/5
3,917,947 A * 11/1975 Fenton ................ G01V 5/0016
378/98.2

(Continued)

FOREIGN PATENT DOCUMENTS

| CN | 1292871 A | 4/2001 |
|---|---|---|
| CN | 1575910 A | 2/2005 |

(Continued)

OTHER PUBLICATIONS

Henke, S., et al., "Identification and Suppression of Thermal Reflections in Inflated Thermal Imaging", Inframation, vol. 5, Jan. 1, 2004, pp. 287-298, XP055039442.

(Continued)

*Primary Examiner* — Gail Kaplan Verbitsky
(74) *Attorney, Agent, or Firm* — Pearne & Gordon LLP

(57) ABSTRACT

A method for detecting metal particles (21) present in a wall (20) of a glass container (2) intended to contain food or pharmaceutical products, said method comprising the steps of: —heating the metal particles (21) present in the wall (20); —inspecting the container (2) during or after said step of heating the metal particles (21) present in the wall (20). The step of heating the metal particles (21) envisages increasing the temperature of the metal particles (21) to a greater extent than the remaining glass parts (22) of the wall (20). The method comprises the step of inspecting the container (2) using means (71) for detecting the metal (Continued)

particles (21) which are hotter than the glass parts (22) of the wall (20).

6 Claims, 2 Drawing Sheets

(56) References Cited

U.S. PATENT DOCUMENTS

| | | | | |
|---|---|---|---|---|
| 4,851,023 | A | * | 7/1989 | Gonzales-Oliver ..... C03C 23/00 65/390 |
| 5,688,418 | A | | 11/1997 | Yoshiyasu et al. |
| 5,969,810 | A | * | 10/1999 | Nicks ................ G01N 21/9036 356/428 |
| 6,013,915 | A | | 1/2000 | Watkins et al. |
| 6,690,016 | B1 | | 2/2004 | Watkins et al. |
| 9,791,395 | B2 | | 10/2017 | Weinstein et al. |
| 10,684,265 | B2 | * | 6/2020 | Burkhalter ................ A61L 2/04 |
| 2004/0131844 | A1 | * | 7/2004 | Shinozaki ................ C08K 3/08 428/328 |
| 2008/0060383 | A1 | * | 3/2008 | Schuller ................ G01N 21/71 65/29.18 |
| 2014/0174127 | A1 | | 6/2014 | Dalstra |
| 2016/0054245 | A1 | | 2/2016 | Weinstein |
| 2019/0210768 | A1 | * | 7/2019 | Adib .................... C08G 73/105 |
| 2020/0375846 | A1 | * | 12/2020 | Chang .................... B32B 17/06 |

FOREIGN PATENT DOCUMENTS

| | | | | | |
|---|---|---|---|---|---|
| CN | | 1696674 | A1 | | 11/2005 |
| CN | | 103308521 | A | | 9/2013 |
| CN | | 20429840 | U | * | 4/2015 |
| CN | | 204298240 | U | * | 4/2015 |
| CN | | 104597081 | A | | 5/2015 |
| CN | | 104634816 | | | 5/2015 |
| CN | | 104359944 | A | | 12/2015 |
| CN | | 105339782 | A | | 2/2016 |
| CN | | 105466945 | A | | 4/2016 |
| DE | | 102013002602 | | | 8/2014 |
| DE | | 102013002602 | A1 | * | 8/2014 ............. G01N 25/72 |
| DE | | 102014005932 | A1 | * | 10/2015 ......... G01N 21/8903 |
| EP | | 2743689 | A1 | | 6/2014 |
| EP | | 2743689 | B1 | | 6/2019 |
| JP | | 2003215077 | A | * | 7/2003 |
| JP | | 2010203897 | A | * | 9/2010 |
| JP | | 5360375 | B2 | * | 12/2013 |
| JP | | 5360380 | B2 | * | 12/2013 |
| JP | | 2017195101 | A1 | * | 10/2017 |
| KR | | 101708147 | B1 | * | 1/2006 |
| KR | | 102015620 | B1 | * | 8/2019 |
| RU | | 2601346 | C2 | * | 11/2016 ........... B07C 5/3408 |
| WO | | WO-2014124754 | A1 | * | 8/2014 ............. G01N 25/72 |
| WO | | WO-2015162303 | A1 | * | 10/2015 ......... G01N 21/8903 |

OTHER PUBLICATIONS

Vavilov, V., et al., "Review of Pulsed Thermal NDT: Physical Principles, Theory and Data Processing", NDT & E International, vol. 73, Apr. 18, 2015, pp. 28-52, XP029158811.

* cited by examiner

METHOD AND APPARATUS FOR DETECTING METAL PARTICLES PRESENT IN A WALL OF A GLASS CONTAINER

TECHNICAL FIELD

The present invention relates to a method for detecting metal particles present in a wall of a glass container and an apparatus that implements such method.

An application of the invention is in the production of glass bottles intended for containing pharmaceutical products. Such bottles are made by moulding through metal dies considering the high temperatures to which the glass is brought. Therefore it cannot be excluded a priori that minuscule metal particles, not visible to the naked eye, can be incorporated into the glass walls.

In some cases such particles can cause the colouring of the product. The colouring of the drug causes alarm among consumers which can lead to the recall of whole batches of bottles with huge economic damage. Furthermore, such metal particles in some rare cases could also determine a reduction in the efficacy of the drug and obviously that is absolutely to be avoided.

The risk, which may only be theoretical, of the metal present in the container being able to be introduced into the body of a person to whom the drug is administered, is also to be avoided.

BACKGROUND ART

Cosmetic inspection systems are known for inspecting bottles which, through video cameras, recognise the presence of defects in the container such as, for example, the presence of chips or impurities visible to the naked eye.

Techniques are also known for checking the correct shaping of the bottle. On this point, the bottle may be heated so as to check with an infrared camera for any abnormal concentrations of the mass of the glass.

Inspection methods are known for inspecting glass products, of the type described in EP2743689, DE102013002602, scientific publication S. Henke et al "Identification and suppression of thermal reflections in infrared thermal imaging".

DISCLOSURE OF THE INVENTION

The object of the present invention is to develop a method and an apparatus for detecting metal particles in a wall of a glass container.

The technical task set and the objects specified are substantially attained by a method and an apparatus for detecting metal particles in a wall of a glass container, comprising the technical characteristics as set out in one or more of the accompanying claims.

BRIEF DESCRIPTION OF DRAWINGS

Further characteristics and advantages of the present invention will more fully emerge from the indicative, and thus non-limiting, description of a method and an apparatus for detecting metal particles illustrated in the accompanying drawings, in which.

DETAILED DESCRIPTION OF PREFERRED EMBODIMENTS OF THE INVENTION

Figure 1:
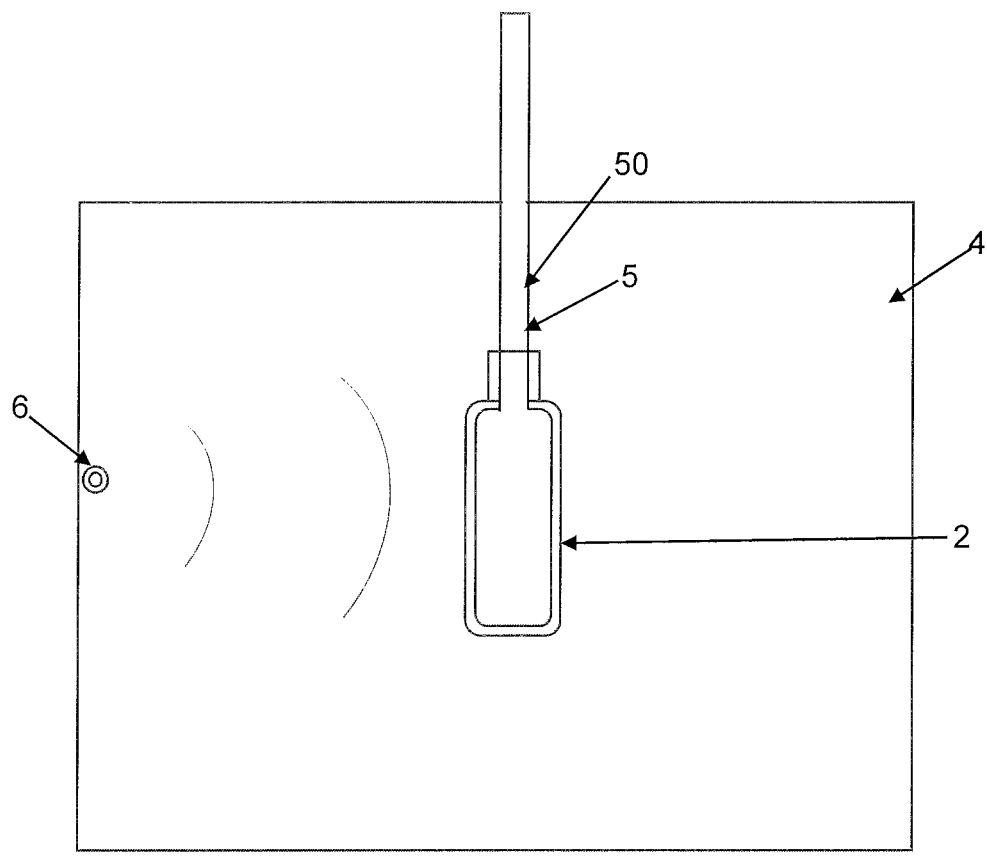
FIGS. 1 and 2 show two successive steps of the method according to the present invention.

The subject matter of the present invention is an apparatus for detecting metal particles present in a wall of a container. In this text wall generally means a lateral wall, but also a bottom or any other part of the container used for defining an internal volume intended to house a product.

The apparatus comprises means 6 for heating the metal particles present in the container. Such heating means 6 brings the metal particles present in the wall to a higher temperature with respect to the remaining glass parts of the wall. This can be obtained by exploiting particular types of heating means 6. In particular, the heating means 6 can comprise induction heating means.

In this case, the induction means is crossed by alternating electric current that generates a magnetic field that heats the container. The magnetic materials are heated more quickly than the non-magnetic ones since the heating therein due to hysteresis is added to the heating due to eddy currents. Any metal particles present in the glass container will therefore create hot points in the glass wall.

In an alternative solution, the heating means 6 may be microwave heating means. Also in this case, the microwaves heat the metal particles to a greater extent than the remaining glass parts of the container.

The apparatus further comprises means 7 for inspecting the container. The inspection means 7 comprises means 71 for detecting hot points of the container which identify said metal particles. The action of the heating means 6 therefore aims to increase the temperature of the metal particles to a greater extent than the remaining parts of the wall so as to facilitate their subsequent recognition. By way of example, the temperature of the metal particles may even be 150° C. higher than the temperature of some glass portions of the container.

In order to facilitate the recognition of the metal particles, the inspection means 7 advantageously comprise at least one filter 72, operatively connected to said detection means 71. The filter 72 may be a polarising filter. The filter 72 highlights predetermined electromagnetic frequencies emitted by the hot points. Advantageously, the filter 72 can be calibrated according to specific requirements. Typically, such filter 72 highlights electromagnetic wavelengths comprised between 400 nm and 5 micron. The detection means 71 could comprise a camera, preferably a high definition one. The inspection means 7 could possibly comprise a thermal camera.

The apparatus comprises means 50 for gripping the container. In an exemplifying and non-limiting solution (see FIGS. 1 and 2) the gripping means 50 may comprise an insert 5 intended to be coupled with interference within a mouth 23 of the container 2. Such coupling is particularly advantageous since in that way the gripping means 50 is not very invasive either during the heating of the product or during the subsequent inspection. Furthermore, in that case, the gripping means 50 superimposes a portion of the container which could however be subject to a future inspection (e.g. upon specific request from the customer).

Figure 2:
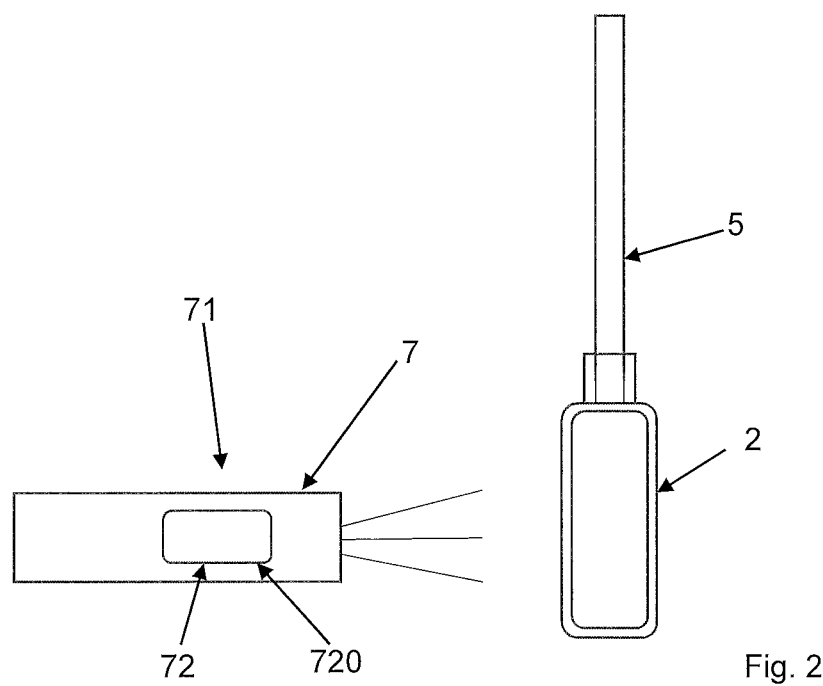
Figure 3:
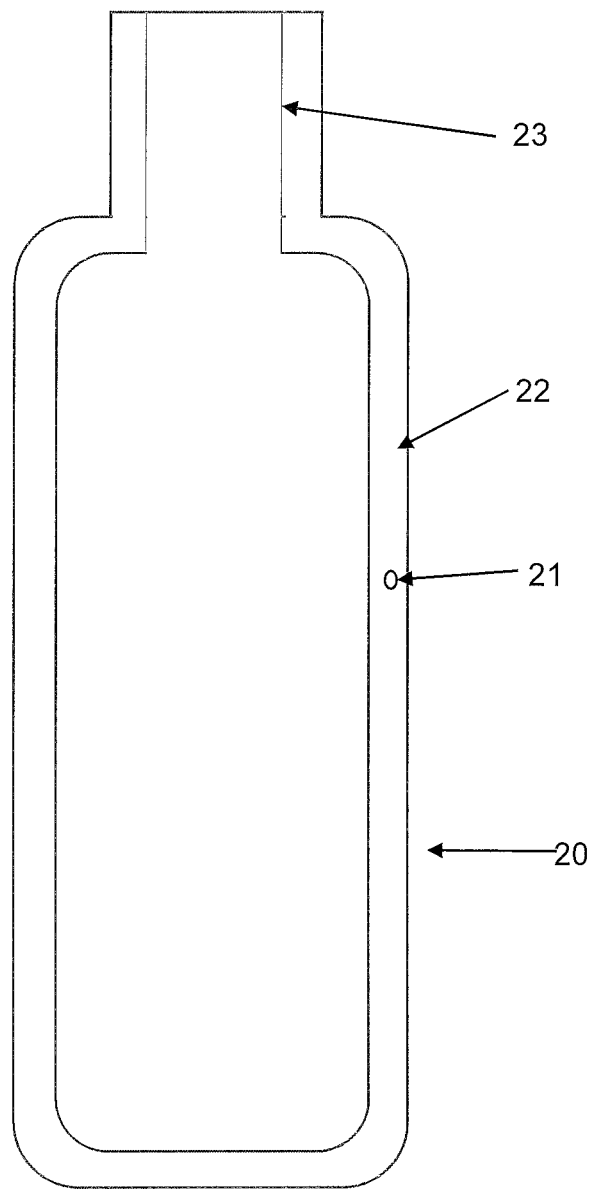
FIG. 3 shows an enlarged view of a container illustrated in FIGS. 1 and 2.

As exemplified in FIG. 1, the heating means 6 comprises a compartment 4 into which the insert 5 is insertable together with the container in order to perform the heating of the metal particles.

The subject matter of the present invention is also a method for detecting metal particles 21 present in a wall 20 of a glass container 2. Advantageously, such container 2 is intended to contain food or pharmaceutical products. A particularly advantageous application is connected with the containment of liquid or powder pharmaceutical products. Conveniently, the method according to the present invention is implemented by an apparatus having one or more of the characteristics described hereinabove.

The method comprises the steps of heating the metal particles 21 present in the wall 20. The step of heating the metal particles 21 envisages increasing the temperature of the metal particles 21 to a greater extent than the remaining glass parts 22 of the wall 20.

This is obtained through specific heating methods for example through induction heating means. In this way, at the end of the heating process, any metal particles will constitute hot points of the container and this will facilitate their identification.

Appropriately, the method envisages gripping the container 2 and inserting it into a compartment 4 in which said step of heating the metal particles present in the wall 20 takes place.

The step of gripping the container 2 envisages introducing an insert 5 into a mouth 23 of the container 2 placing said insert 5 in interference with the mouth 23 of the container 2.

On this point, the method comprises inspecting the container 2 during or after said step of heating the metal particles 21 present in the wall 20.

Such inspection step takes place when the metal particles 21 have a higher temperature than ambient temperature.

In fact, the method comprises the step of inspecting the container 2 using means 71 for detecting said metal particles 21 which are hotter than the glass parts 22 of the wall 20. This allows metal particles having dimensions greater than 50 micrometres to be traced, in particular comprised between 60 and 100 micrometres (dimensions in which the particles are not visible to the naked eye). Appropriately, the step of inspecting the container envisages moving the detection means 71 with respect to the container itself. For example, the inspection means 71 can be raised or lowered for better analysing corresponding parts of the container; the container 2 can also be rotated to offer distinct faces to the detection means 71.

Appropriately, the step of inspecting the container 2 can comprise the step of highlighting the metal particles 21 that are hotter than the glass parts 22 through at least one polarising filter 720. Such highlighting can take place, for example, by using different tones in an image provided by the detection means 71.

The step of inspecting the container 2 can comprise the step of isolating predetermined electromagnetic wavelengths emitted by the metal particles that are hotter than the glass parts 22. Appropriately, such electromagnetic frequencies are comprised between 400 nm and 5 micron.

In a particular solution, the step of gripping the container takes place through the same gripping means 50 that support the container 2 both during the step of heating the metal particles 21 and during the step of inspecting the container 2.

Possibly, during the step of inspecting the container 2, the latter could initially be gripped in a first zone and then in a second zone so as to prevent missing the inspection of specific parts (hidden by the gripping means 50).

The invention as it is conceived enables achieving multiple advantages. Above all, it allows any metal particles present in the glass walls of the containers and not visible to the naked eye to be highlighted. This allows containers that have detectable metal particles or however containers in which the quantity of metal particles is unacceptable to be discarded. All this has important effects as it ensures that the product cannot be in any way altered by metal particles and prevents huge damage to companies by averting the recall of entire production batches due to individual faulty containers.

The invention as it is conceived is susceptible to numerous modifications and variants, all falling within the scope of the inventive concept characterising it. Further, all the details can be replaced with other technically-equivalent elements. In practice, all the materials used, as well as the dimensions, can be any according to requirements.

The invention claimed is:

1. A method for detecting metal particles (21) present in a wall (20) of a glass container intended to contain food or pharmaceutical products, said method being characterised in that it comprises the steps of:
   heating the metal particles (21) present in the wall (20);
      the step of heating the metal particles (21) envisages increasing the temperature of the metal particles (21) to a greater extent than the remaining glass parts (22) of the wall (20);
   inspecting the container (2) during or after said step of heating the metal particles (21) present in the wall (20);
      the step of inspecting the container (2) envisaging inspecting the container (2) through means (70) for detecting the metal particles (21) which are hotter than the glass parts (22) of the wall (20);
   the step of heating the metal particles (21) present in the wall (20) comprising the step of heating said container (2) through induction heating means or through microwave heating means; the step of inspecting the container comprises the step of detecting the metal particles that are hotter than the glass parts (22) using at least one polarising filter (720).

2. A method for detecting metal particles (21) present in a wall (20) of a glass container intended to contain food or pharmaceutical products, said method being characterised in that it comprises the steps of:
   heating the metal particles (21) present in the wall (20);
      the step of heating the metal particles (21) envisages increasing the temperature of the metal particles (21) to a greater extent than the remaining glass parts (22) of the wall (20);
   inspecting the container (2) during or after said step of heating the metal particles (21) present in the wall (20);
   the step of inspecting the container (2) envisaging inspecting the container (2) through means (70) for detecting the metal particles (21) which are hotter than the glass parts (22) of the wall (20);
   the step of heating the metal particles (21) present in the wall (20) comprising the step of heating said container (2) through induction heating means or through microwave heating means; the step of inspecting the container (2) comprising the step of isolating predetermined electromagnetic frequencies emitted by the metal particles (21) that are hotter than the glass parts (21).

3. The method according to claim 1, characterised in that the container (2) is gripped and inserted into a compartment (4) in which said step of heating the metal particles present in the wall (20) takes place.

4. The method according to claim 3, characterised in that the step of gripping the container (2) envisages introducing an insert (5) into a mouth (23) of the container (2) placing said insert (5) in interference with the mouth (23) of the container (2).

5. The method according to claim 1, characterised in that the step of inspecting the container (2) using said detection means (70) enables the metal particles (21) that have dimensions comprised between 60 and 100 micrometres to be identified.

6. An apparatus for detecting metal particles present in a wall of a container comprising:
- means (6) for heating the metal particles present in the wall of the container;
- means (7) for inspecting the container;

the means (7) for inspecting comprising means (71) for detecting hot points of the wall of the container which identify said metal particles (21);

characterised in that said heating means (6) comprises induction heating means or heating means through microwaves; the means (7) for inspecting comprising at least one filter (72), operatively connected to said detection means (71), for detecting predetermined electromagnetic frequencies emitted by the hot points.

\* \* \* \* \*